(12) United States Patent  
Buttermilch et al.

(10) Patent No.: US 6,585,771 B1  
(45) Date of Patent: Jul. 1, 2003

(54) DEVICE FOR HANDLING BALL HEADS OF JOINT PROSTHESES

(75) Inventors: Manek Buttermilch, Berlin (DE); Ernst Hoch, Notzingen (DE); Hartmut Kalberer, Hochdorf (DE); Paul Silberer, Waghausel (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/646,707

(22) PCT Filed: Mar. 26, 1999

(86) PCT No.: PCT/EP99/02246

§ 371 (c)(1),  
(2), (4) Date: Nov. 28, 2000

(87) PCT Pub. No.: WO99/48436

PCT Pub. Date: Sep. 30, 1999

(30) Foreign Application Priority Data

Mar. 26, 1998 (DE) .......................................... 198 13 328

(51) Int. Cl.⁷ .................................................. A61F 2/32
(52) U.S. Cl. .................................. 623/22.12; 623/21.11
(58) Field of Search ................... 623/22.11, 22.12–22.2, 623/23.11–23.14

(56) References Cited

U.S. PATENT DOCUMENTS 4,542,825 A * 9/1985 Thomas et al. .............. 206/363  
5,133,765 A * 7/1992 Cuilleron .................... 260/363

FOREIGN PATENT DOCUMENTS

EP 0 373 078 * 6/1990  
EP 0684025 A1 11/1995

* cited by examiner

Primary Examiner—Paul B. Prebilic  
Assistant Examiner—Hieu Phan  
(74) Attorney, Agent, or Firm—Antonelli, Terry, Stout & Kraus, LLP

(57) ABSTRACT

A protective cap for prosthetic joints having one element in the form of a ball head, especially in the case of hip end-prosthetic joints, protects the ball head when it is positioned and fixed on the cone of the shank by the surgeon by hand. A crown is arranged on the pole of the protective cap. The crown is in the form of a plate for, the shape of the plate and its extent relative to the protective cap being such that it is possible to grip behind the plate on the side that faces the protective cap.

15 Claims, 3 Drawing Sheets

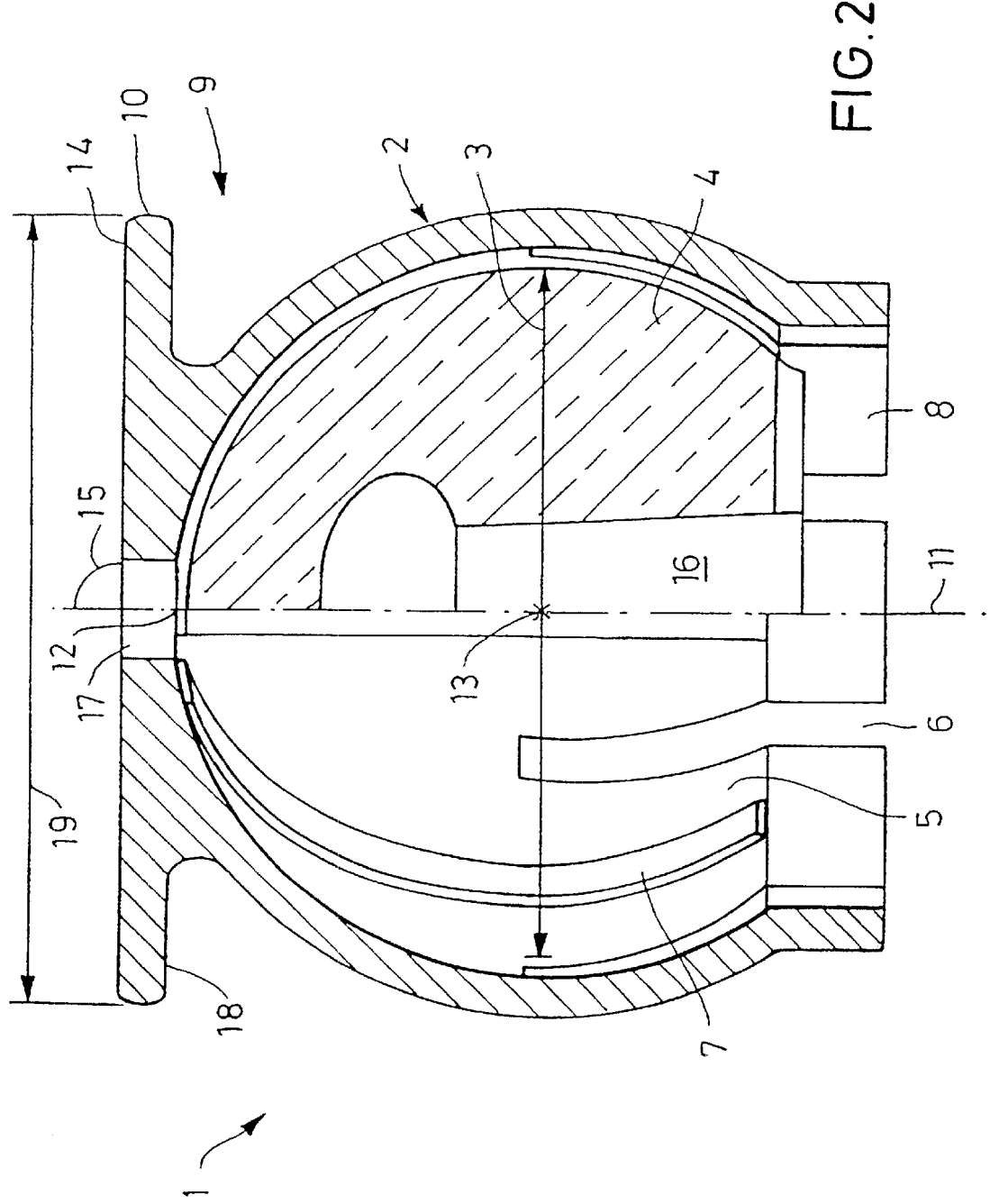

DEVICE FOR HANDLING BALL HEADS OF JOINT PROSTHESES

BACKGROUND OF THE INVENTION

The invention relates to a device for handling ball heads of prosthetic joints.

Prosthetic joints in which one joint element is in the form of a socket and the other joint element is in the form of a ball head which is mounted rotatably in the socket are known especially as shoulder and hip prosthetic joints. Such prostheses are usually of modular design. Hip endo-prosthetic joints, for example, consist of the socket, which is inserted into the hip bone, and the shank, which is inserted into the thigh bone. The shank has a pin, the so-called cone, onto which the ball head is pushed. Especially in that modularly designed endo-prosthesis, implant components of various materials and sizes are combined with one another in order to provide adaptation to the physical build of the patient. For example, ball heads made of a cobalt/chromium alloy or of an aluminium oxide ceramics material are pushed onto a cone made of a titaniumr or cobalt/chromium/molybdenum alloy. The technique used for connecting metal or ceramics ball heads to the cone is press-fit connection, especially a conical press fit. In that technique, the ball head, which has a conical bore, is placed on the cone. Once the ball head has been pushed onto the cone, it is fixed in place by an impact to the ball head.

As is known from the publication "Das Prinzip der Konus-Steckverbindung für keramische Kugelköpfe bei Hüftendoprothesen" [The principle of the conical socket connection for ceramics ball heads in hip endo-prostheses] by G. Willmann, Mat.-wiss. U. Werkstofftech. 24, pages 315–319 (1993), all ceramics materials are brittle. In the case of loads that are not applied over an area and in the event of damage to the surface as a result of scratches, concentrations of stress may occur, resulting in the destruction of the ball head. In metal ball heads, scratches may occur which may in turn cause friction in the surrounding socket.

In order to protect the ball heads from damage until they are used in the operating theatre, it is known to provide them with a protective cap that is matched to the shape of the ball. In the case of ball heads that differ only slightly in diameter, protective caps having the same internal diameter are used. The protective caps are usually removed only in the operating theatre. In its lower region, a protective cap is divided into blades which engage around the ball head to below its equatorial diameter and thus automatically hold the protective cap on the ball head. The ball heads of hip endo-prosthetic joints are positioned on the shank by the surgeon by hand. For that purpose, the protective cap must be removed, which is difficult in the vicinity of the surgical wound because the surgeon's gloves will be wet with bodily fluids. As the ball head is being positioned, its polished surface may become scratched by residues on the gloves. In the case of metal ball heads, this can result in increased friction in the socket. Moreover, there is an additional risk of damaging the surface of the ball heads because of the large number of instruments that are used during an operation. A further difficulty during the operation lies in reliably identifying ball heads that differ only very slightly in diameter.

BRIEF SUMMARY OF THE INVENTION

The problem underlying the present invention is therefore to construct the protective caps so that handling of the ball heads during the operation is facilitated, protection of the ball heads is provided also while the shank is being pushed onto the cone and the possibility of distinguishing between different sizes and materials is improved.

The problem is solved by means of a device for handling ball heads of prosthetic joints, in which the surface of each ball head is covered by a protective cap to beyond the equatorial diameter before being positioned on the cone of a shank, so that the protective cap is held automatically on the ball head and can be removed without a tool, characterized in that there is arranged on the pole of the protective cap a crown in the form of a plate, and the shape of the plate and its extend relative to the protective cap are such that it is possible to grip behind the plate on the side facing the protective cap.

On the pole of the protective cap, which is intended to protect the ball head against damage from the time of its manufacture until it is to be used, the device according to the invention for handling ball heads has a crown in the form of a plate. The shape of the plate and its extent relative to the protective cap are such that it is possible to grip behind the plate on the side facing the protective cap. The plate may be round or polygonal, or may alternatively have a different circumferential shape.

Whilst it is very difficult during the operation for a surgeon to remove a conventional protective cap on a ball head with gloves that are wet with bodily fluids and whilst the ball head is difficult to handle because of its polished surface, the device according to the invention for handling ball heads allows the ball head to be held securely until it is positioned on the shank and to be guided reliably. The crown allows the ball head to be positioned by its conical opening onto the cone of the shank in a targeted manner. The surface on the plate of the crown may additionally serve as an impact surface for the fixing tool with which the ball head is pressed onto the cone by an impact. The plate offers a larger surface area for the impact tool to strike than does the curved surface of a ball. The sensitive, polished surface of the ball is also protected against damage caused by the impact tool.

During the entire handling operation until fixing on the cone of the shank has been effected, the surface of the ball head is constantly protected against damage caused by surgical tools or by contamination. Once the ball head has been fixed on the cone of the shank, the protective cap can be removed easily from the ball head by means of the crown that can be gripped from behind. During removal, the blades of the protective cap expand and release the ball head. The material of the device can be, for example, a tough impact-resistant plastics material.

In an advantageous development of the invention, the plate is so arranged that it lies perpendicular to the connecting line extending from the centre point of the ball head to the pole of the protective cap. This enables the device for handling ball heads to be aligned with the cone of the shank. The surface of the plate may be flat or slightly convexly curved. As a result, it can also serve as an impact surface for the fixing tool.

In a further advantageous development of the invention, a neck may be arranged between the protective cap and the plate of the crown. Such a neck, which may be, for example, about 1 cm in length, further facilitates the possibility of gripping the plate from behind and, thus, handling. The neck also provides the possibility of specifically directing the fixing force to the ball. As the ball head is positioned on the cone of the shank, the force applied by the fixing impact is directed precisely in the longitudinal direction of the cone when the neck is aligned precisely in the longitudinal direction of the cone.

The neck may also extend in the form of a rod and may be, for example, up to 100 mm in length. A device for handling ball heads of such construction can be used, for example, for ball heads that have not been delivered already covered with a protective cap. In preparation for the operation, those ball heads can be inserted into such a handling device. The rod then acts as an alignment and insertion aid for the surgeon. Because of the length of the rod, that device provides very good scope for positioning and placing on the shank.

A ball head can be positioned easily on the cone of a shank when the centre line of the conical opening of the ball head is so aligned that it extends through the pole of the protective cap of the handling device according to the invention. When the crown has a neck or a rod for the plate, these may be aligned in the direction of the cone. The cone and the opening in the ball head are thus in alignment with one another and the ball head needs only to be pushed onto the cone.

In a further development of the invention, the diameter of the plate may have a particular relationship with the diameter of the ball head in question. As a result, it is possible to give an indication of the diameter of the ball head by virtue of a plate diameter that has been determined beforehand relative to the diameter of the ball head. It is thus considerably easier for the surgeon to distinguish between ball heads of different diameters during the operation.

The possibility of distinguishing between ball heads can be increased still further in a further development of the invention wherein the surface of the plate that is remote from the protective cap bears an identification marker. That identification marker may be written or engraved on, or may be a coloured identification marker. The identification marker can provide information, for example, relating to the material of the ball head, its diameter, the type and size of its conical bore and the batch data and manufacturer. The surgeon would thus be better and more reliably able to distinguish between ball heads.

The invention will be explained in greater detail with reference to embodiments.

BRIEF DESCRIPTION OF THE SEVERAL VIEWS OF THE DRAWINGS

FIG. 2 is a section through the device, which has been positioned on a ball head, the ball head also being shown in section;

DETAILED DESCRIPTION OF THE INVENTION

Figure 1:
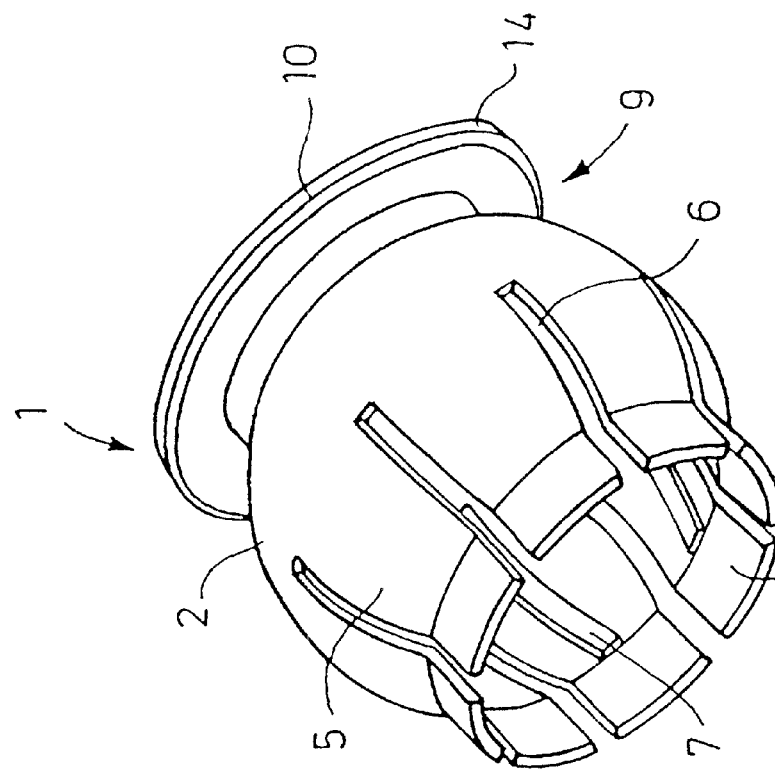
FIG. 1 is a perspective view of a device according to the invention for handling ball heads.

FIG. 1 is an enlarged perspective view in which the reference numeral 1 denotes a device according to the invention for handling ball heads. The protective cap 2, which, as shown in a still further enlarged view in FIG. 2, covers the ball head 4, is divided, from about the equatorial diameter 3 of the ball head 4, into uniformly wide blades 5 which are separated from one another by slits 6. In the present embodiment, eight uniformly wide blades 5 are distributed around the circumference of the protective cap 2, the blades 5 engaging around the ball head 4 beyond the equatorial diameter 3. Each of the blades 5 is reinforced by a web 7. The web 7 also ensures that only a small surface area of each of the blades 5 rests against the surface of the ball head 4. As a result, the contact area of the protective cap 2 and also the friction exerted on the ball surface is small. At their lower end, the blades 5 each have a ring-forming projection 8. Those ring-forming projections 8 make it easier to push the protective cap 2 onto a ball head.

According to the invention, the protective cap 2 has a crown 9 in the form of a plate 10. The circumference of the plate 10, which is in this case circular, can alternatively be polygonal, or can be of any other shape. The diameter 19 of the plate 10 can be so chosen that it can be related to the diameter 3 of the ball head 4. The smaller the diameter 19 is, for example, the smaller is the diameter of the ball head.

FIG. 2 is a section through the device 1 according to the invention for handling ball heads according to FIG. 1. The protective cap 2 has been positioned on a ball head 4 which is also shown in section but is not shown in the left-hand half of the protective cap. With reference to the sectional view, it can be seen that, in the present embodiment, the plate 10 with its flat surface 14 is arranged perpendicular, at a right angle 15, to the connecting line 11 extending from the centre point 13 of the ball head 4 to the pole 12 of the protective cap 2. The connecting line 11 between the pole 12 of the protective cap 2 and the centre point 13 of the ball head 4 is at the same time the centre line of the conical bore 16 in the ball head 4 for receiving the cone on the shank. As an ideal precondition for positioning on the cone, the centre line of the conical bore 11 extends through the pole 12 of the protective cap 2. This makes it considerably easier to position the ball head on the cone and to fix it by striking the plate 10 with an impact tool. Owing to the manner of manufacture, the crown 9 has an opening 17 that extends in the direction of the centre line 11, which is the connecting line between the centre point 13 of the ball head 4 and the pole 12 of the protective cap 2.

The extent 19 of the plate 10 relative to the protective cap 2 is such that it is possible to grip behind the plate on the side 18 facing the protective cap 2. Its extent can correspond, for example, to about the largest external diameter of the protective cap 2.

Figure 3:
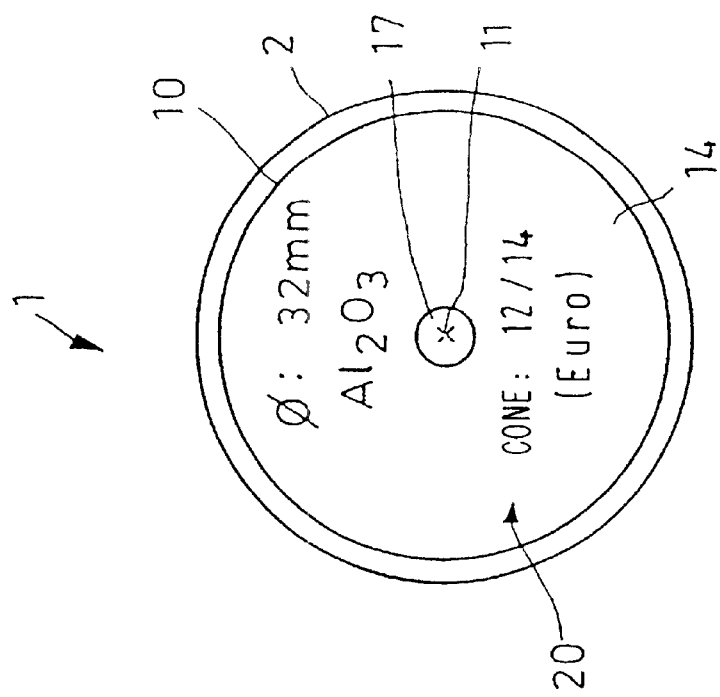
FIG. 3 is a plan view of the plate.

FIG. 3 is a plan view onto the surface 14 of the plate 10. It will be seen that the surface 14 bears an identification marker 20. The surface 14 may be provided, for example, with text that gives information relating to the diameter (in the present case 32 mm), the material (in the present case $Al_2O_3$), and the type of cone (in the present case a Euro cone 12/14).

The text may be applied by printing or stamping. Coloured markings can also be provided, or the material, preferably an impact-resistant plastics material, can be dyed.

Figure 4:
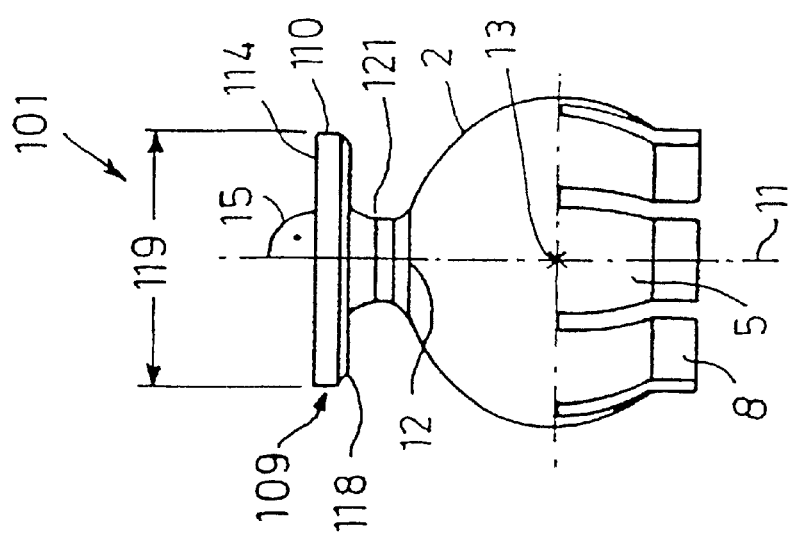
FIG. 4 shows a further handling device having a neck between the plate and the protective cap.

The embodiment in FIG. 4 shows a device 101 for handling ball heads that differs from the preceding embodiment in that, in the case of the crown 109 on the protective cap 2, a neck 121 is arranged between the protective cap 2 and the plate 110. Features that are unaltered with respect to the preceding embodiment are denoted by the same reference numerals.

As a result of the greater distance between the plate 110 and the protective cap 2, it is considerably easier to grip behind the side 118 of the plate 110 of the crown 109.

Accordingly, the diameter 119 of the plate 110 can, for example, be smaller than in the preceding embodiment.

Figure 5:
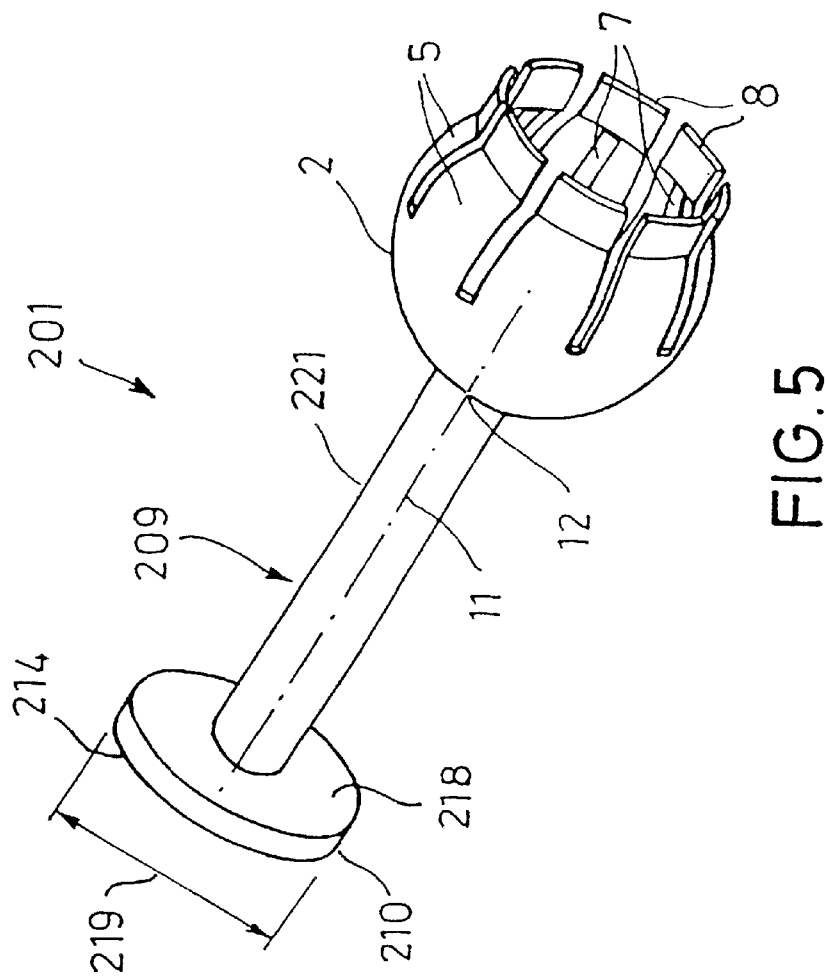
FIG. 5 shows a handling device having a rod between the plate and the protective cap.

In the embodiment according to FIG. 5, the device 201 for handling ball heads has between the protective cap 2 and the plate 210 a neck that extends in the form of a rod 221 and may be up to 100 mm in length. With such a handling aid, it is possible to position and insert the ball heads especially easily and precisely.

What is claimed is:

1. Device for handling ball heads of prosthetic joints, comprising a protective cap covering the surface of each ball head to beyond the equatorial diameter before being positioned on the cone of a shank, so that the protective cap is held automatically on the ball head and is removed without a tool after the ball head is attached to the cone of the shank, and a crown arranged on the pole of the protective cap in the form of a plate, the shape of the plate and its extent relative to the protective cap being such that it is possible to grip behind the plate on the side facing the protective cap.

2. Device according to claim 1, characterized in that the plate is arranged perpendicular to the connecting line extending from the center point of the ball head to the pole of the protective cap.

3. Device according to claim 1, characterized in that a neck is arranged between the protective cap and the plate.

4. Device according to claim 3, characterized in that the neck extends in the form of a rod.

5. Device according to claim 4, characterized in that the rod is up to 100 mm in length.

6. Device according to claim 1, characterized in that the connecting line between the center point of the ball head and the pole of the protective cap is at the same time the center line of the conical bore in the ball head.

7. Device according to claim 1, characterized in that the diameter of the plate has a predetermined relationship with the diameter of the ball head.

8. Device according to claim 1, characterized in that the surface of the plate that is remote from the protective cap bears an identification marker.

9. Device according to claim 1, wherein the plate has a flat top surface arranged perpendicular to a connecting line extending from a center point of the ball head to the pole of the protective cap, the flat top surface forming a striking surface for an impact tool used to attach the ball head on cone of the shank.

10. A device for handling a ball head of a prosthetic joint, comprising:

a protective cap to cover the ball head to beyond the equatorial diameter of the ball head, the protective cap having an internal shape substantially corresponding to an external shape of the portion of the ball head to be covered by the protective cap and comprising a plurality of blades extending from the pole of the protective cap and distributed around the circumference of the cap, the blades being separated from each other at lower ends opposite the pole; and a crown provided at the pole of the protective cap, the crown including a plate having a dimension, measured perpendicular to a connecting line extending from a center point of the ball head to the pole of the protective cap, relative to the protective cap at the pole such that it is possible to grip behind the plate on a side facing the protective cap.

11. The device according to claim 10, wherein the blades are separated from one another by slits extending from about the portion of the protective cap to cover the equatorial diameter of the ball had to the lower ends of the blades.

12. The device according to claim 10, further comprising a reinforcing web on an internal surface of each blade for limiting the surface area of each blade permitted to touch the ball head.

13. The device according to claim 10, wherein the plate has a circular cross-section, the diameter of which corresponds to about the largest external diameter of the protective cap.

14. The device according to claim 10, wherein the plate has a flat top surf ace arranged perpendicular to the connecting line connecting the center point of the ball head to the pole of the protective cap.

15. The device according to claim 10, wherein the crown further includes a neck arranged between the pole of the protective cap and the plate.

* * * * *